(12) United States Patent
Russo (10) Patent No.: US 10,653,232 B1
(45) Date of Patent: May 19, 2020

(54) HAND SANITIZER HOLSTER (71) Applicant: Paula Russo, Tampa, FL (US)

(72) Inventor: Paula Russo, Tampa, FL (US)

( * ) Notice: Subject to any disclaimer, the term of this patent is extended or adjusted under 35 U.S.C. 154(b) by 0 days.

(21) Appl. No.: 16/133,748

(22) Filed: Sep. 18, 2018

(51) Int. Cl.
*A45F 5/02* (2006.01)
*A61L 2/00* (2006.01)

(52) U.S. Cl.
CPC .............. *A45F 5/02* (2013.01); *A61L 2/0082* (2013.01)

(58) Field of Classification Search
CPC .... A45F 5/00; A45F 5/02; A45F 5/022; A45F 2005/002; A61L 2/0082; A61L 2/0088
USPC ......................................................... 222/175
See application file for complete search history.

(56) References Cited

U.S. PATENT DOCUMENTS

| | | | | |
|---|---|---|---|---|
| 4,331,271 A | * | 5/1982 | Anderson | A45F 5/00 224/150 |
| 4,526,298 A | * | 7/1985 | Boxer | A45F 3/16 222/130 |
| 4,722,464 A | * | 2/1988 | Wright | G11B 33/025 224/235 |
| 5,002,214 A | * | 3/1991 | Caranci | A45F 5/02 224/240 |
| 5,060,835 A | * | 10/1991 | Payne | A45C 1/04 224/148.2 |
| D323,430 S | * | 1/1992 | Niederkorn | 224/221 |
| 5,148,949 A | * | 9/1992 | Luca | A01K 27/006 222/175 |
| 5,211,321 A | * | 5/1993 | Rodriguez | A41D 13/0012 2/102 |
| 5,263,618 A | * | 11/1993 | Talavera | A45F 3/14 224/148.2 |
| D386,256 S | * | 11/1997 | Turpin | D22/125 |
| 5,683,012 A | * | 11/1997 | Villaveces | A45F 5/02 222/175 |
| 5,692,661 A | * | 12/1997 | Kellerman | A45F 5/00 224/646 |
| 5,927,548 A | * | 7/1999 | Villaveces | A45F 5/02 222/175 |
| 6,234,357 B1 | * | 5/2001 | Lewis | A45F 5/02 222/175 |
| 6,241,135 B1 | * | 6/2001 | Thatcher | A45F 3/16 222/175 |
| 6,283,334 B1 | * | 9/2001 | Mahaffey | A45F 5/02 222/175 |

(Continued)

FOREIGN PATENT DOCUMENTS

GB 2451156 1/2009

*Primary Examiner* — Nicholas J. Weiss
(74) *Attorney, Agent, or Firm* — Kyle A. Fletcher, Esq.

(57) ABSTRACT

The hand sanitizer holster is a garment. The hand sanitizer holster comprises a belt, a fastening structure, and a plurality of primary holsters. The fastening structure secures the belt to a healthcare worker. The plurality of primary holsters attach to the belt. Each of the plurality of primary holsters contains a chemical container filled with a sanitizer. The sanitizer is an anti-microbial chemical used for cleaning the hands of the healthcare worker. Each holster contained within the plurality of primary holsters is configured such that the sanitizer dispenses from the chemical container without removing the chemical container from the holster. In a second potential embodiment of the disclosure, the hand sanitizer holster further comprises a shoulder harness. The shoulder harness further comprises one or more straps and one or more secondary holsters.

17 Claims, 6 Drawing Sheets

(56) References Cited

U.S. PATENT DOCUMENTS

| | | | |
|---|---|---|---|
| 6,568,575 B1* | 5/2003 | Bartholomew | A45F 3/14 224/258 |
| 6,644,527 B1* | 11/2003 | Karenga | A41D 13/0012 2/1 |
| 6,684,413 B2* | 2/2004 | Cascioli | A45F 3/14 2/312 |
| 6,698,632 B1* | 3/2004 | Turner, Jr. | A45F 5/021 224/196 |
| 6,923,357 B2* | 8/2005 | Smith | A01K 97/06 224/251 |
| 7,334,714 B2* | 2/2008 | Brown | A45C 13/30 224/600 |
| 7,617,952 B2* | 11/2009 | Saleh | A47K 5/1202 222/103 |
| D631,648 S | 2/2011 | Pullin | |
| 7,988,020 B2* | 8/2011 | Shoham | A61B 90/80 222/175 |
| 8,341,765 B2* | 1/2013 | Brodbeck | A41D 7/00 2/67 |
| 8,747,008 B2 | 6/2014 | Geesbreght | |
| 8,757,443 B2* | 6/2014 | Pelfrey | B65D 51/248 222/113 |
| 8,973,788 B1* | 3/2015 | Burns | A47K 5/1201 220/751 |
| 9,027,795 B2* | 5/2015 | Zaima | A61L 2/26 222/175 |
| 9,289,051 B1* | 3/2016 | Capps | A45F 5/02 |
| 10,264,859 B2* | 4/2019 | Parker | A44C 9/0069 |
| 2003/0230613 A1* | 12/2003 | Karenga | A45F 3/14 224/602 |
| 2003/0230614 A1* | 12/2003 | Karenga | A41D 13/0012 224/602 |
| 2007/0075091 A1* | 4/2007 | Tombazzi | A45F 3/16 222/82 |
| 2007/0205235 A1* | 9/2007 | Knight | A45F 5/00 224/223 |
| 2008/0017683 A1* | 1/2008 | Votel | A45F 5/02 224/677 |
| 2008/0083785 A1* | 4/2008 | Nelson | A45F 5/02 222/175 |
| 2008/0135588 A1* | 6/2008 | Haines | A45F 5/02 224/148.1 |
| 2008/0203127 A1* | 8/2008 | Castillo-Garrison | A45C 13/30 224/607 |
| 2009/0250494 A1* | 10/2009 | Studer | A45F 5/02 224/257 |
| 2011/0011886 A1* | 1/2011 | Zaima | A61L 2/26 222/1 |
| 2011/0284601 A1* | 11/2011 | Pullin | A45C 11/00 224/251 |
| 2013/0048678 A1* | 2/2013 | Carrasco Salazar | B05B 15/62 222/175 |
| 2013/0119096 A1* | 5/2013 | Morgan | A45F 3/005 224/148.1 |
| 2013/0168408 A1 | 7/2013 | Kubicz | |
| 2015/0216367 A1* | 8/2015 | Barbier | A47K 5/1201 222/1 |
| 2017/0265633 A1* | 9/2017 | Foley | A45F 5/00 |
| 2019/0106264 A1* | 4/2019 | Kinarti | A45F 5/021 |

* cited by examiner

HAND SANITIZER HOLSTER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including chemical substances used for disinfecting objects other than foodstuffs and contact lenses, more specifically, an accessory therefor. (A61L2/0082).

Hand washing and hand sanitization are the first and primary tools used in maintaining the sanitation of a healthcare environment. Most modern medical facilities maintain wall mounted pump stations of a hand sanitizer that allow a healthcare worker to clean their hands between patient contact sessions. Unfortunately, the dynamic environment of the healthcare system often presents unplanned practicalities, such as emergency situations or carrying objects, which prevent a healthcare worker from accessing the mounted pump station in a timely manner. Clearly, an apparatus that improves the ability of a healthcare worker to access a hand sanitizer would be of benefit to a healthcare worker.

SUMMARY OF INVENTION

The hand sanitizer holster is a garment. The hand sanitizer holster is worn over the outerwear of a healthcare worker. The hand sanitizer holster comprises a belt, a fastening structure, and a plurality of primary holsters. The fastening structure secures the belt to the healthcare worker. The plurality of primary holsters attach to the belt. Each of the plurality of primary holsters attach to the belt such that the each of the plurality of primary holsters is within easy reach of the healthcare worker. Each of the plurality of primary holsters contains a chemical container filled with a sanitizer. The sanitizer is an anti-microbial chemical used for cleaning the hands of the healthcare worker. Each holster contained within the plurality of primary holsters is configured such that the sanitizer dispenses from the chemical container without removing the chemical container from the holster. In a second potential embodiment of the disclosure, the hand sanitizer holster further comprises a shoulder harness. The shoulder harness further comprises one or more straps and one or more secondary holsters.

These together with additional objects, features and advantages of the hand sanitizer holster will be readily apparent to those of ordinary skill in the art upon reading the following detailed description of the presently preferred, but nonetheless illustrative, embodiments when taken in conjunction with the accompanying drawings.

In this respect, before explaining the current embodiments of the hand sanitizer holster in detail, it is to be understood that the hand sanitizer holster is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the hand sanitizer holster.

It is therefore important that the claims be regarded as including such equivalent construction insofar as they do not depart from the spirit and scope of the hand sanitizer holster. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
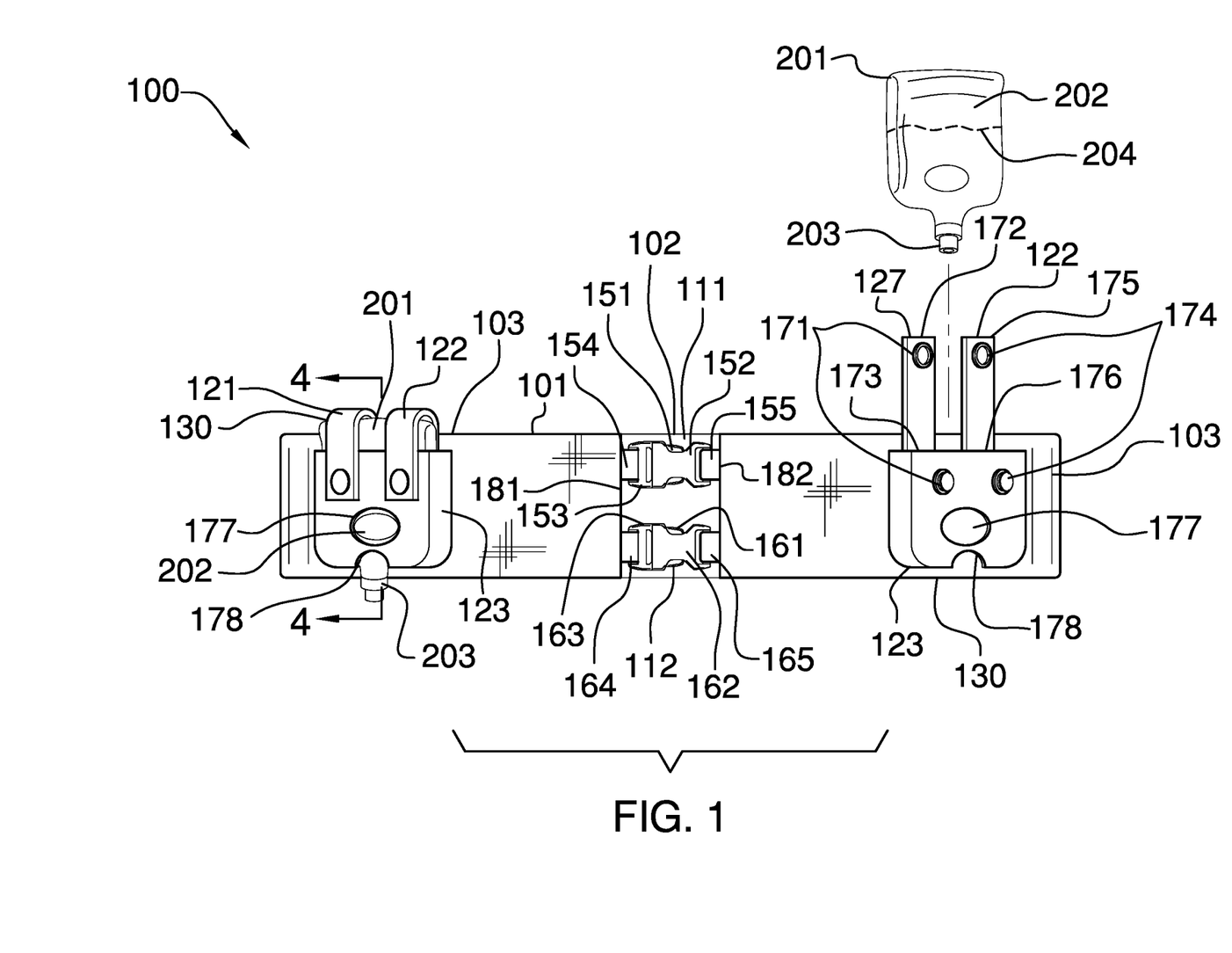
FIG. 1 is a front view of an embodiment of the disclosure.
Figure 2:
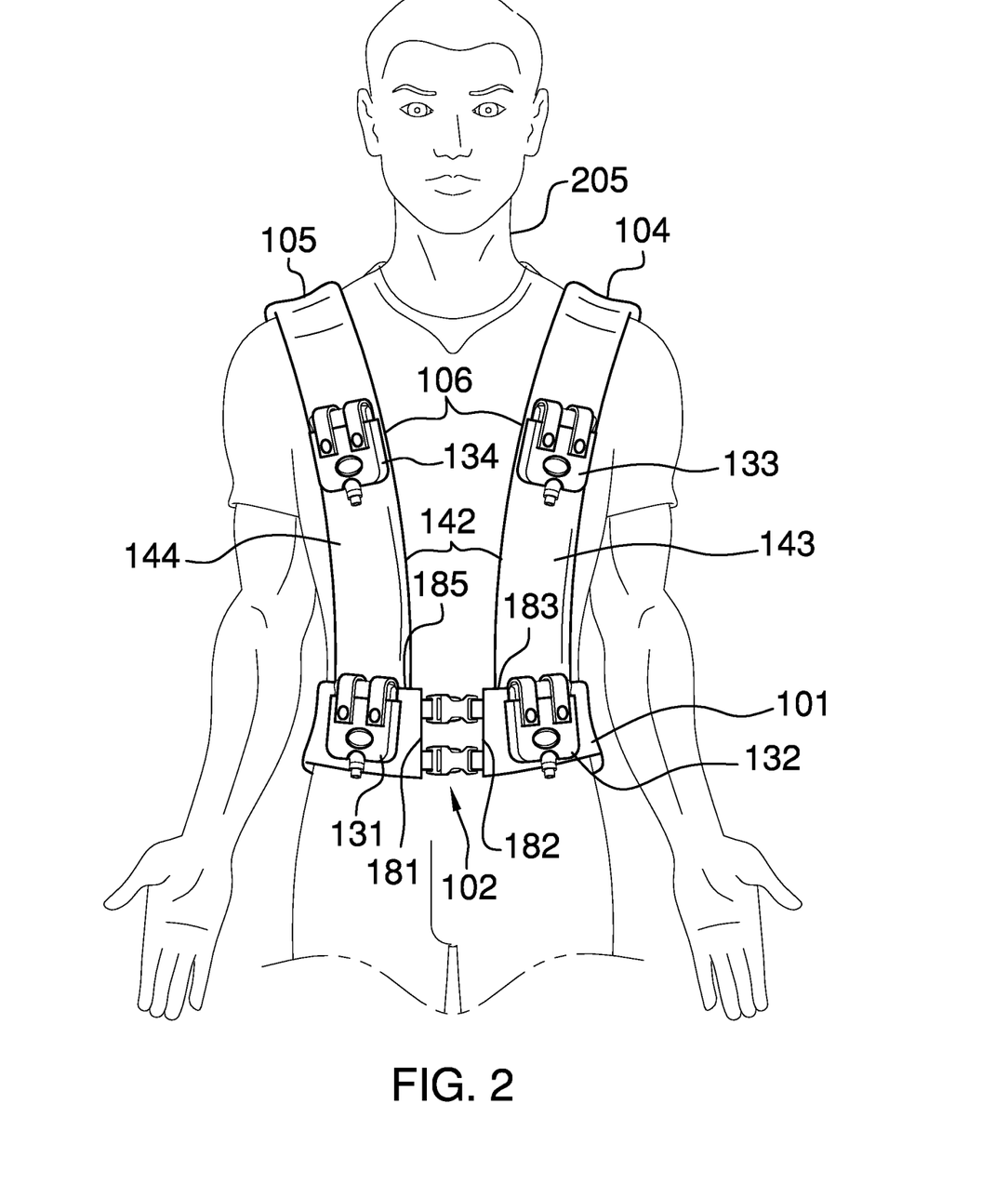
FIG. 2 is an in-use view of an alternative embodiment of the disclosure.
Figure 3:
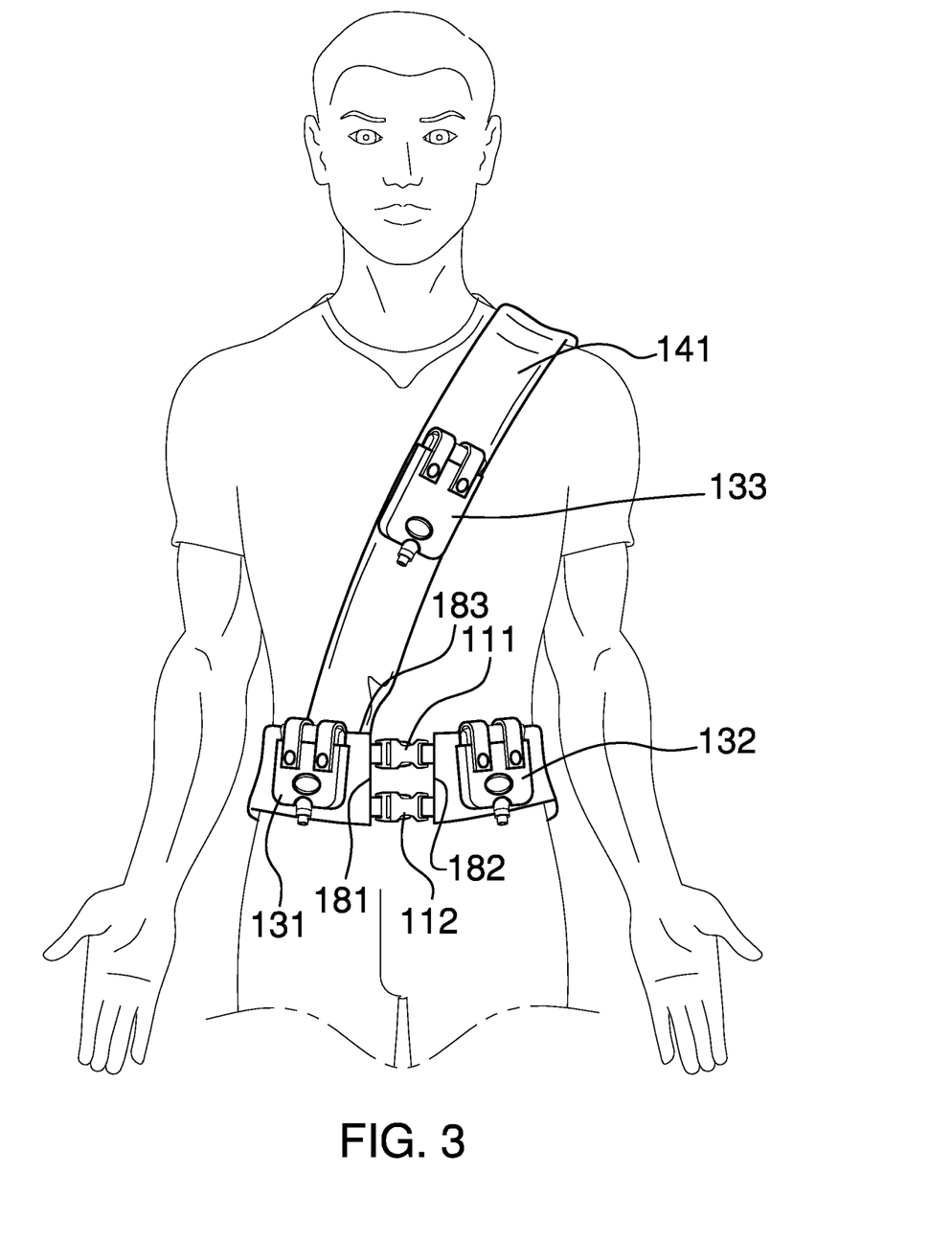
FIG. 3 is an in-use view of an alternative embodiment of the disclosure.
Figure 4:
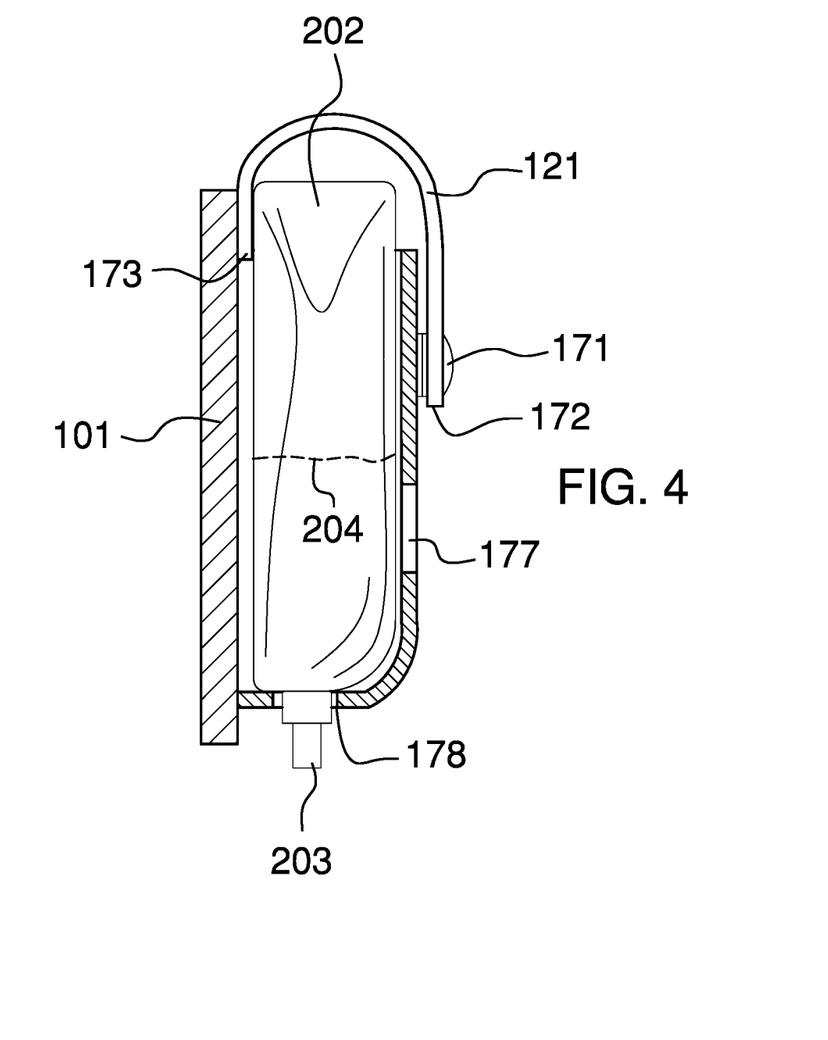
FIG. 4 is a cross-sectional view of an embodiment of the disclosure across 4-4 as shown in FIG. 1.
Figure 5:
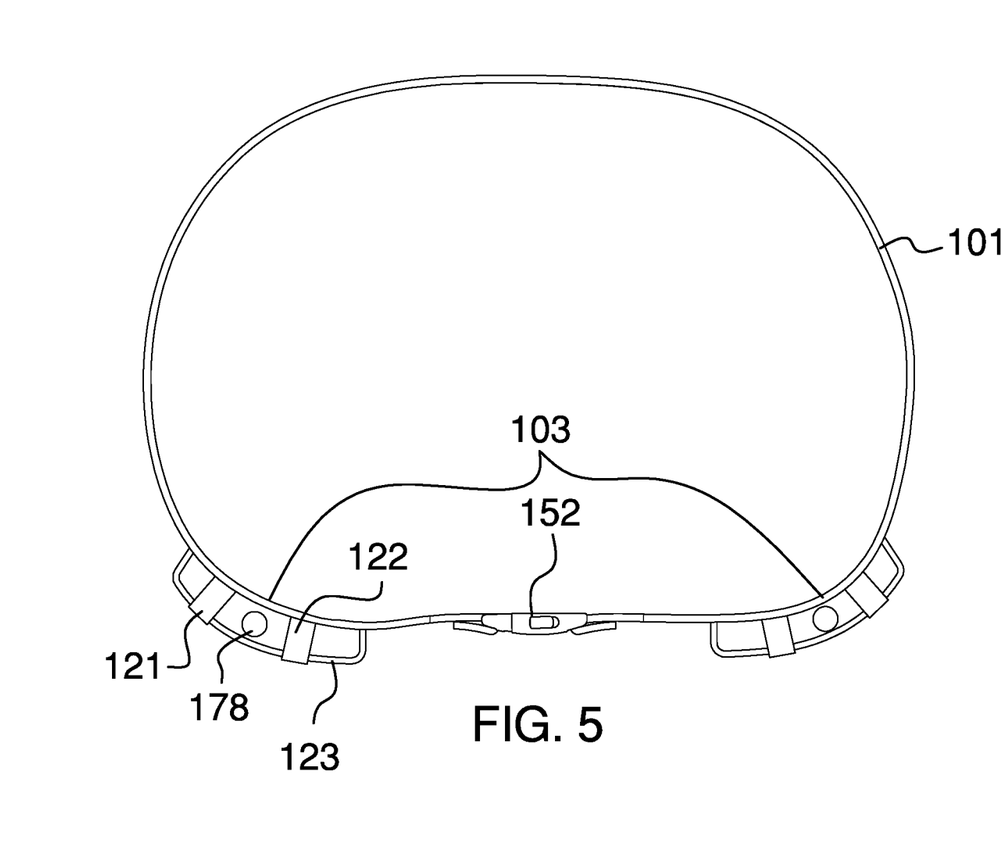
FIG. 5 is a top view of an embodiment of the disclosure.
Figure 6:
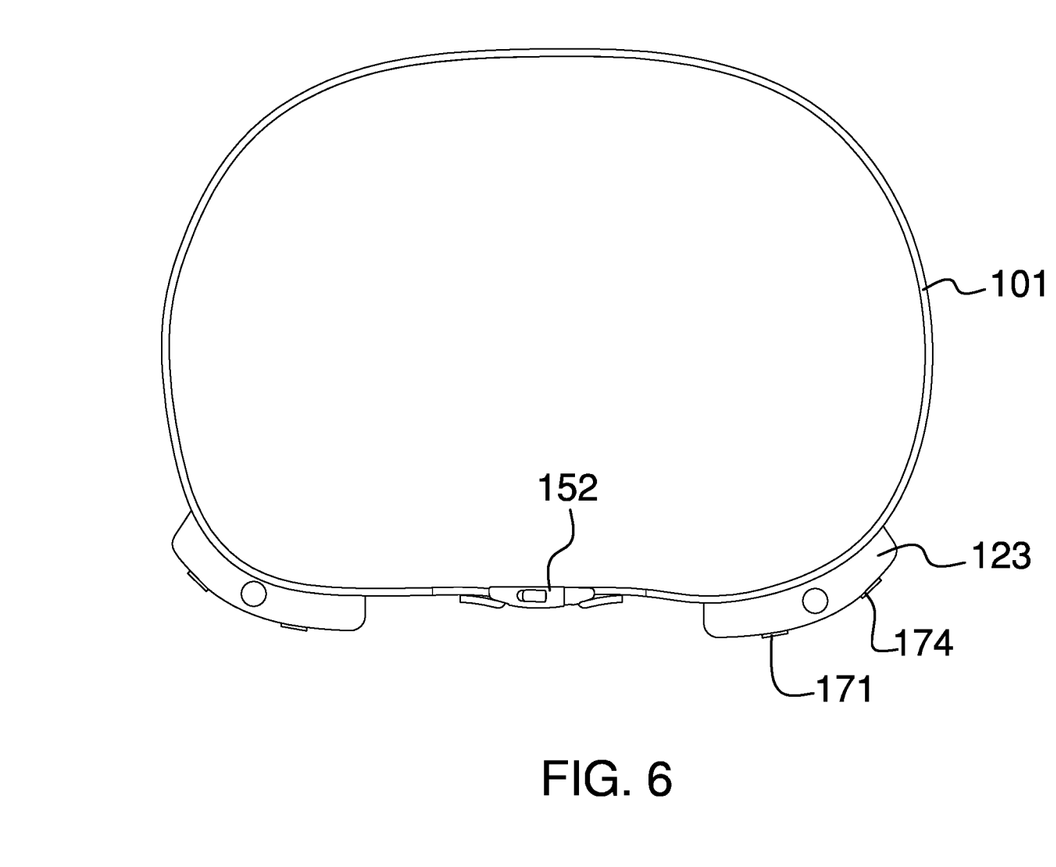
FIG. 6 is a bottom view of an embodiment of the disclosure.

Detailed reference will now be made to one or more potential embodiments of the disclosure, which are illustrated in FIGS. 1 through 6.

The hand sanitizer holster 100 (hereinafter invention) is a garment. The invention 100 is worn over the outerwear of a healthcare worker 205. The invention 100 comprises a belt 101, a fastening structure 102, and a plurality of primary holsters 103. The fastening structure 102 secures the belt 101 to the healthcare worker 205. The plurality of primary holsters 103 attach to the belt 101. Each of the plurality of primary holsters 103 attach to the belt 101 such that the each of the plurality of primary holsters 103 is within easy reach of the healthcare worker 205. Each of the plurality of primary holsters 103 contains a chemical container 201 filled with a sanitizer 204. The sanitizer 204 is an antimicrobial chemical used for cleaning the hands of the healthcare worker 205. Each holster contained within the plurality of primary holsters 103 is configured such that the sanitizer 204 dispenses from the chemical container 201 without removing the chemical container 201 from the holster.

The chemical container 201 is a containment device configured to store and dispense a sanitizer 204. The chemical container comprises a bottle 202 and a nozzle 203. The bottle 202 is a semi-rigid structure with an elastic nature. The bottle 202 forms the containment vessel of the chemical container 201. The nozzle 203 is a device that forms a port through which the sanitizer 204 is dispensed. The bottle 202 and the nozzle 203 are well-known and documented structures. The sanitizer 204 is a cleansing fluid used to clean the hands of the healthcare worker 205. The sanitizer 204 comprises a chemical intended to eliminate microorganisms. In the first potential embodiment of the disclosure, the chemical intended to eliminate microorganisms is selected from the group consisting of 2-pyrrolidinone with iodine (CAS 25655-41-8), 5-chloro-2-(2,4-dichlorophenoxy)-phenol (CAS 3380-34-5), N-(4-chlorophenyl)-N'-(3,4-dichlorophenyl)-urea (CAS 101-20-2), and alcohol.

The belt 101 is a commercially available webbing. The belt 101 is worn around the waist of the healthcare worker 205. The belt 101 attaches the plurality of primary holsters 103 to the waist of the healthcare worker 205. The belt 101 is further defined with a first end 181 and a second end 182.

The fastening structure 102 is a commercially available fastening device. The fastening structure 102 removably secures the belt 101 to the waist of the healthcare worker 205. In the first potential embodiment of the disclosure, the fastening structure 102 is formed from one or more quick release buckles. The fastening structure 102 comprises a first quick release buckle 111 and a second quick release buckle 112.

The first quick release buckle 111 is a commercially available quick release buckle. The first quick release buckle 111 attaches the first end 181 of the belt 101 to the second end 182 of the belt 101. The first quick release buckle 111 further comprises a first male connector 151, a first female connector 152, a first ring and slider arrangement 153, a first adjustment strap 154, and a second adjustment strap 155.

The first male connector 151 is the male component of the first quick release buckle 111. The first female connector 152 is the female component of the first quick release buckle 111. The first ring and slider arrangement 153 is a well-known, documented, and commercially available device used to adjust the effective length of the belt 101 around the waist of the healthcare worker 205. The first ring and slider arrangement 153 is provisioned with the belt 101. The first ring and slider arrangement 153 attaches to the first male connector 151 and the first adjustment strap 154 such that the span of the length of the first quick release buckle 111 is adjustable. The first adjustment strap 154 is a commercially available webbing that attaches the first male connector 151 of the first quick release buckle 111 to the first end 181 of the belt 101. The second adjustment strap 155 is a commercially available webbing that attaches the first female connector 152 of the first quick release buckle 111 to the second end 182 of the belt 101.

The second quick release buckle 112 is a commercially available quick release buckle. The second quick release buckle 112 attaches the first end 181 of the belt 101 to the second end 182 of the belt 101. The second quick release buckle 112 further comprises a second male connector 161, a second female connector 162, a second ring and slider arrangement 163, a third adjustment strap 164, and a fourth adjustment strap 165.

The second male connector 161 is the male component of the second quick release buckle 112. The second female connector 162 is the female component of the second quick release buckle 112. The second ring and slider arrangement 163 is a well-known, documented, and commercially available device used to adjust the effective length of the belt 101 around the waist of the healthcare worker 205. The second ring and slider arrangement 163 is provisioned with the belt 101. The second ring and slider arrangement 163 attaches to the second male connector 161 and the third adjustment strap 164 such that the span of the length of the second quick release buckle 112 is adjustable. The third adjustment strap 164 is a commercially available webbing that attaches the second male connector 161 of the second quick release buckle 112 to the first end 181 of the belt 101. The fourth adjustment strap 165 is a commercially available webbing that attaches the second female connector 162 of the second quick release buckle 112 to the second end 182 of the belt 101.

A ring and slider arrangement is defined in more detail elsewhere in this disclosure.

Each of the plurality of primary holsters 103 is a holster configured for use in containing a chemical container 201 of sanitizer 204. Each of the plurality of primary holsters 103 attaches to the belt 101 such that the contained chemical container 201 is readily accessible to the healthcare worker 205. Each of the plurality of primary holsters 103 are identical. Each of the plurality of primary holsters 103 are sized to receive a chemical container 201 containing sanitizer 204. Each of the plurality of primary holsters 103 are configured such that the sanitizer 204 dispenses from the chemical container 201 without requiring the removal of the chemical container 201 from the selected primary holster. The plurality of primary holsters 103 comprises a collection of individual holsters 130.

The individual holster 130 is a holster selected from a group of holsters consisting of the plurality of primary holsters 103 and the one or more secondary holsters 106. The individual holster 130 is a structure that contains a single chemical container 201 such that the sanitizer 204 contained within the chemical container 201 is dispensable from the chemical container 201 by the healthcare worker 205 while the chemical container 201 is contained within the individual holster 130. Each individual holster 130 comprises a pouch 123, a first binding strap 121, and a second binding strap 122.

The pouch 123 is a hollow rectangular blocks structure. The inner dimensions of the pouch 123 are greater than the outer dimension of the chemical container 201 such that the chemical container 201 will fit within the hollow interior of the pouch 123. The pouch 123 is formed with an open face such that the chemical container 201 inserts into the pouch 123 through the open face. The open face of the pouch 123 forms the superior surface of the pouch 123 when the invention 100 is worn normally. The pouch 123 further comprises a pressure aperture 177 and a nozzle aperture 178.

The pressure aperture 177 is an aperture formed through a face of the pouch 123 selected from the group consisting of all faces of the pouch 123 except the open face and the face of the pouch 123 that is distal from the open face of the pouch 123. The pressure aperture 177 provides an access port that allows the healthcare worker 205 to provide pressure to the chemical container 201 such that the sanitizer 204 is dispensed from the chemical container 201 through the nozzle 203. The nozzle aperture 178 is an aperture formed through the face of the pouch 123 that is distal from the open face of the pouch 123. The nozzle aperture 178 forms a port through which the nozzle 203 of the bottle 202 inserts.

The first binding strap 121 is a commercially available webbing. The first binding strap 121 attaches to the pouch 123 such that the first binding strap 121 lays over the open face of the pouch 123. The first binding strap 121 secures the chemical container 201 within the hollow interior of the pouch 123. The first binding strap 121 further comprises a first fastener 171. The first binding strap 121 is further defined with a first free end 172 and a first fixed end 173.

The first fixed end 173 is the end of the first binding strap 121 that attaches to the pouch 123. The first free end 172 is the end of the first binding strap 121 that is distal from the first fixed end 173. The first free end 172 remains unattached to the pouch 123 until the first fastener 171 attaches the first free end 172 to the pouch 123. Attaching the first free end 172 to the pouch 123 secures the chemical container 201 within the pouch 123. In the first potential embodiment of the disclosure, the first fastener 171 is selected from the group consisting of a snap and a hook and loop fastener.

The second binding strap 122 is a commercially available webbing. The second binding strap 122 attaches to the pouch 123 such that the second binding strap 122 lays over the open face of the pouch 123. The second binding strap 122 secures the chemical container 201 within the hollow interior of the pouch 123. The second binding strap 122 further comprises a second fastener 174. The second binding strap 122 is further defined with a second free end 175 and a second fixed end 176.

The second fixed end 176 is the end of the second binding strap 122 that attaches to the pouch 123. The second free end 175 is the end of the second binding strap 122 that is distal from the second fixed end 176. The second free end 175 remains unattached to the pouch 123 until the second fastener 174 attaches the second free end 175 to the pouch 123. Attaching the second free end 175 to the pouch 123 secures the chemical container 201 within the pouch 123. In the first potential embodiment of the disclosure, the second fastener 174 is selected from the group consisting of a snap and a hook and loop fastener.

The plurality of primary holsters 103 comprises a first holster 131 and a second holster 132. The first holster 131 is a holster selected from the plurality of primary holsters 103 that attaches to the belt 101. A sewn seam attaches the first holster 131 to the belt 101. The second holster 132 is a holster selected from the plurality of primary holsters 103 that attaches to the belt 101. A sewn seam attaches the second holster 132 to the belt 101.

In a second potential embodiment of the disclosure, the invention 100 further comprises a shoulder harness 104. The shoulder harness 104 further comprises one or more shoulder straps 105 and one or more secondary holsters 106.

The shoulder harness 104 is a harness that attaches to the belt 101. The shoulder harness 104 is worn over one or more shoulders of the healthcare worker 205 such that the shoulder harness 104 supports the belt 101. Each of the one or more shoulder straps 105 is a strap that secures the belt 101 to a shoulder of the healthcare worker 205. The shoulder harness 104 further comprises one or more shoulder straps 105 and one or more secondary holsters 106.

Each of the one or more secondary holsters 106 is a holster configured for use in containing a chemical container 201 of sanitizer 204. Each of the one or more secondary holsters 106 are identical. Each of the one or more secondary holsters 106 is identical to any primary holster selected from the plurality of primary holsters 103. Each of the one or more secondary holsters 106 attaches to the one or more shoulder straps 105. The one or more secondary holsters 106 comprises a third holster 133 and a fourth holster 134.

Each of the one or more shoulder straps 105 is a webbing structure that attaches to the belt 101. The one or more shoulder straps 105 is selected from the group consisting of a cross strap 141 and a plurality of shoulder straps 142.

The cross strap 141 is a commercially available webbing. The cross strap 141 forms the shoulder harness 104 of the invention 100. The cross strap 141 attaches to the belt 101 at two locations. The cross strap 141 attaches to the belt 101 such that: a) the cross strap 141 is supported by a shoulder of the healthcare worker 205; and, b) the cross strap 141 crosses diagonally across the chest of the healthcare worker 205. The cross strap 141 is further defined with a third end 183 and a fourth end. The third end 183 is the edge of the cross strap 141 with the minimum span of distance. The third end 183 attaches to the face of the belt 101 using a sewn seam. The cross strap 141 further comprises a third holster 133. The third holster 133 is a holster selected from the one or more secondary holsters 106 that attaches to the cross strap 141. A sewn seam attaches the third holster 133 to the cross strap 141.

The plurality of shoulder straps 142 forms the shoulder harness 104 of the invention 100. The plurality of shoulder straps 142 further comprises a dexter strap 143, a sinister strap 144, a third holster 133, and a fourth holster 134. The dexter strap 143 is further defined with a third end 183 and a fourth end. The sinister strap 144 is further defined with a fifth end 185 and a sixth end.

The third end 183 is the edge of the dexter strap 143 with the minimum span of distance. The third end 183 attaches to the face of the belt 101 using a sewn seam. The fourth end is the edge of the dexter strap 143 that is distal from the third end 183. The fourth end attaches to the face of the belt 101 using a sewn seam. The fifth end 185 is the edge of the sinister strap 144 with the minimum span of distance. The fifth end 185 attaches to the face of the belt 101 using a sewn seam. The sixth end is the edge of the sinister strap 144 that is distal from the fifth end 185. The sixth end attaches to the face of the belt 101 using a sewn seam.

The dexter strap 143 is a commercially available webbing. The dexter strap 143 forms a portion of the shoulder harness 104 of the invention 100. The dexter strap 143 attaches to the belt 101 at two locations. The dexter strap 143 attaches to the belt 101 such that the dexter strap 143 is supported by the dexter shoulder of the healthcare worker 205.

The sinister strap 144 is a commercially available webbing. The sinister strap 144 forms a portion of the shoulder harness 104 of the invention 100. The sinister strap 144 attaches to the belt 101 at two locations. The sinister strap 144 attaches to the belt 101 such that the sinister strap 144 is supported by the sinister shoulder of the healthcare worker 205.

The third holster 133 is a holster selected from the one or more secondary holsters 106 that attaches to the dexter strap 143. A sewn seam attaches the third holster 133 to the dexter strap 143. The fourth holster 134 is a holster selected from the one or more secondary holsters 106 that attaches to the sinister strap 144. A sewn seam attaches the fourth holster 134 to the sinister strap 144.

The following definitions were used in this disclosure:

2-pyrrolidinone with iodine: As used in this disclosure, 2-pyrrolidinone with iodine (CAS 25655-41-8) is an antiseptic chemical substance commonly referred to as povidone-iodine.

5-chloro-2-(2,4-dichlorophenoxy)-phenol: As used in this disclosure, 5-chloro-2-(2,4-dichlorophenoxy)-phenol (CAS 3380-34-5) is an antifungal and antibiotic agent that is commonly used in consumer products. 5-chloro-2-(2,4-dichlorophenoxy)-phenol is commonly referred to as triclosan. See N-(4-chlorophenyl)-N'-(3,4-dichlorophenyl)-urea.

Alcohol: As used in this disclosure, an alcohol refers to an organic chemical structure that comprises a hydroxyl functional group.

Anchor: As used in this disclosure, anchor means to hold an object firmly or securely.

Anchor Point: As used in this disclosure, an anchor point is a location to which a first object can be securely attached to a second object.

Bottle: As used in this disclosure, a bottle is a container used for the storage of fluids. Access to the interior of a bottle is gained through the neck of the bottle. The neck is an elongated tube that forms an aperture through which fluids can be introduced and removed from the bottle.

Buckle: As used in this disclosure, a buckle is a fastening device used for joining a first loose end of a strap to a second loose end of the same strap or a different strap. A buckle further comprises a male connector that is attached to a first loose end and a female connector that is attached to a second loose end. The male connector has a pin or other structure that is generally caught by a structure formed in the female connector.

Dexter: As used in this disclosure, dexter is a directional reference that refers to the right side of the body or the right side of an object from the perspective of a viewer who is facing the posterior side of the object.

Fastener: As used in this disclosure, a fastener is a device that is used to join or affix two objects. Fasteners generally comprise a first element which is attached to the first object and a second element which is attached to the second object such that the first element and the second element join to removably attach the first object and the second object. Common fasteners include, but are not limited to, hooks, zippers, magnets, snaps, buttons, buckles, quick release buckles, or hook and loop fasteners.

Functional Group: As used in this disclosure, a functional group is a specific chemical structure that 1) defines the structure of a chemical family; and, 2) determines the properties of the chemical family. Common functional groups include, but are not limited to, aldehydes, alkanes, alkenes, alkynes, alcohols, amides, amines, carboxylic acids, esters, ethers, haloalkanes, haloalkenes, haloalkynes, and ketones. As a practical matter, the intention of this definition is to use the term functional group in the same manner as the term is commonly used in organic chemistry.

Harness: As used in this disclosure, a harness is an apparatus comprising a plurality of straps and one or more fasteners that is used to fasten or anchor a first person or first object to a second object. The phrase N point harness refers to the installation of the harness wherein the harness has N anchor points. For example, a two-point harness has two anchor points while a five-point harness has five anchor points.

Holster: As used in this disclosure, a holster is a storage pouch that attaches to a belt, webbing, sling, or luggage item. The holster is dedicated to containing a previously identified object such that the previously identified object is readily accessible.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook/loop surface" with the understanding that when the two objects are fastened together one of the two objects will have a hook surface and the remaining object will have the loop surface.

Hydroxyl: As used in this disclosure, a hydroxyl refers to a functional group comprising the chemical formulation OH. The hydroxyl is the primary functional group that forms alcohols. When unbonded, the hydroxyl is considered an ion and is considered to be a radical.

Inferior: As used in this disclosure, the term inferior refers to a directional reference that is parallel to and in the same direction as the force of gravity when an object is positioned or used normally.

Inner Dimension: As used in this disclosure, the term inner dimension describes the span from a first inside or interior surface of a container to a second inside or interior surface of a container. The term is used in much the same way that a plumber would refer to the inner diameter of a pipe.

Microorganism: As used in this disclosure, a microorganism is an organism too small to be viewed by the unaided eye. Microorganisms are typically single-celled organisms such as bacteria, yeast, viruses, protozoa, fungi, and algae.

N-(4-chlorophenyl)-N'-(3,4-dichlorophenyl)-urea: As used in this disclosure, N-(4-chlorophenyl)-N'-(3,4-dichlorophenyl)-urea (CAS 101-20-2) is an antibacterial agent commonly found in soaps. N-(4-chlorophenyl)-N'-(3,4-dichlorophenyl)-urea is commonly called triclocarban.

Nozzle: As used in this disclosure, a nozzle is a device that receives fluid under pressure and releases the fluid in a controlled manner into an environment.

Organic: As used in this disclosure, organic refers to a carbon-based chemical structure. A limited number of carbon-based salts are traditionally considered inorganic chemical structure and are excluded from the study of organic chemistry.

Outer Dimension: As used in this disclosure, the term outer dimension describes the span from a first exterior or outer surface of a tube or container to a second exterior or outer surface of a tube or container. The term is used in much the same way that a plumber would refer to the outer diameter of a pipe.

Quick Release Buckle: As used in this disclosure, a quick release buckle is a specific type of buckle wherein the buckle can be readily and easily disconnected by pressing a button or pinching one of the ends of the quick release buckle. Quick release buckles are readily and commercially available.

Rectangular Block: As used in this disclosure, a rectangular block refers to a three-dimensional structure comprising six rectangular surfaces (commonly called faces) formed at right angles. Within this disclosure, a rectangular block may further comprise rounded edges and corners.

Ring and Slider Arrangement: As used in this disclosure, a ring and slider arrangement is an apparatus comprising a ring component and a slider component that is used to adjust the effective length of a webbing in an application. In the ring and slider arrangement, an end of the webbing is inserted through the slider component, looped through the ring component and then reverse threaded through the slider component for a second time. By adjusting the position of the slider component relative to the webbing, the effective length of the webbing can be adjusted. Ring and slider arrangements are well known and documented in the textile arts.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Sinister: As used in this disclosure, sinister is a directional reference that refers to the left side of the body or the left side of an object from the perspective of a viewer who is facing the posterior side of the object.

Snap: As used in this disclosure, a snap is a fastener that comprises a male component and a female component. The snap is engaged by pressing the male component into the female component.

Strap: As used in this disclosure a strap is a strip of leather, cloth, or other flexible material, often with a buckle, that is used to fasten, secure, carry, or hold onto something.

Strip: As used in this disclosure, the term describes a long and narrow object of uniform thickness that appears thin relative to the length of the object. Strips are often rectangular in shape.

Superior: As used in this disclosure, the term superior refers to a directional reference that is parallel to and in the opposite direction of the force of gravity when an object is positioned or used normally.

Textile: As used in this disclosure, a textile is a material that is woven, knitted, braided or felted. Synonyms in common usage for this definition include fabric and cloth.

Waist: As used in this disclosure, the waist refers to the perimeter around the abdomen of a person. Traditionally, the perimeter formed by the waist is closer to the hips than the ribs of the person.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips. Webbings have tensile strength but are too flexible to provide compressive strength and are not suitable for use in pushing objects.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An accessory for dispensing a chemical substance comprising
   a belt, a fastening structure, and a plurality of primary holsters;
   wherein the fastening structure secures the belt to a healthcare worker;
   wherein the plurality of primary holsters attach to the belt;
   wherein the accessory for dispensing a chemical substance is a garment;
   wherein the accessory for dispensing a chemical substance is worn over the outerwear of a healthcare worker;
   wherein each of the plurality of primary holsters attach to the belt;
   wherein each of the plurality of primary holsters contains a chemical container filled with a sanitizer;
   wherein the chemical container is a containment device configured to store and dispense a sanitizer;
   wherein each holster contained within the plurality of primary holsters is configured such that the sanitizer dispenses from the chemical container without removing the chemical container from the holster;
   wherein each individual holster comprises a pouch, a first binding strap, and a second binding strap;
   wherein the first binding strap and the second binding strap attach to the pouch;
   wherein the pouch is a hollow rectangular blocks structure;
   wherein the inner dimensions of the pouch are greater than the outer dimension of the chemical container such that the chemical container will fit within the hollow interior of the pouch;
   wherein the pouch is formed with an open face such that the chemical container inserts into the pouch through the open face;
   wherein the open face of the pouch forms the superior surface of the pouch;
   wherein the pouch further comprises a pressure aperture and a nozzle aperture;
   wherein the pressure aperture is an aperture formed through a face of the pouch selected from the group consisting of all faces of the pouch except the open face and the face of the pouch that is distal from the open face of the pouch;
   wherein the nozzle aperture is an aperture formed through the face of the pouch that is distal from the open face of the pouch.

2. The accessory for dispensing a chemical substance according to claim 1
   wherein the chemical container comprises a bottle and a nozzle;
   wherein the bottle is a semi-rigid structure with an elastic nature;

wherein the bottle forms the containment vessel of the chemical container;

wherein the nozzle is a device that forms a port through which the sanitizer is dispensed;

wherein sanitizer is selected from the group consisting of 2-pyrrolidinone with iodine (CAS 25655-41-8), 5-chloro-2-(2,4-dichlorophenoxy)-phenol (CAS 3380-34-5), N-(4-chlorophenyl)-n'-(3,4-dichlorophenyl)-urea (CAS 101-20-2), and alcohol.

3. The accessory for dispensing a chemical substance according to claim 2 wherein the belt is a webbing;

wherein the belt attaches the plurality of primary holsters to the waist of the healthcare worker;

wherein the belt is further defined with a first end and a second end.

4. The accessory for dispensing a chemical substance according to claim 2 wherein the fastening structure is a fastening device;

wherein the fastening structure removably secures the belt to the healthcare worker.

5. The accessory for dispensing a chemical substance according to claim 4 wherein each of the plurality of primary holsters attaches to the belt such that the contained chemical container is readily accessible to the healthcare worker;

wherein each of the plurality of primary holsters are identical;

wherein each of the plurality of primary holsters are configured such that the sanitizer dispenses from the chemical container without requiring the removal of the chemical container from the selected primary holster.

6. The accessory for dispensing a chemical substance according to claim 5 wherein the fastening structure comprises a first quick release buckle and a second quick release buckle;

wherein the first quick release buckle attaches the first end of the belt to the second end of the belt;

wherein the second quick release buckle attaches the first end of the belt to the second end of the belt.

7. The accessory for dispensing a chemical substance according to claim 6 wherein the first quick release buckle further comprises a first male connector, a first female connector, a first ring and slider arrangement, a first adjustment strap, and a second adjustment strap;

wherein the first ring and slider arrangement adjusts the effective length of the belt;

wherein the first adjustment strap is a webbing that attaches the first male connector of the first quick release buckle to the first end of the belt;

wherein the second adjustment strap is a webbing that attaches the first female connector of the first quick release buckle to the second end of the belt;

wherein the first ring and slider arrangement is provisioned with the belt;

wherein the first ring and slider arrangement attaches to the first male connector and the first adjustment strap such that the span of the length of the first quick release buckle is adjustable.

8. The accessory for dispensing a chemical substance according to claim 7 wherein the second quick release buckle further comprises a second male connector, a second female connector, a second ring and slider arrangement, a third adjustment strap, and a fourth adjustment strap;

wherein the second male connector is the male component of the second quick release buckle;

wherein the second female connector is the female component of the second quick release buckle;

wherein the third adjustment strap is a webbing that attaches the second male connector of the second quick release buckle to the first end of the belt;

wherein the fourth adjustment strap is a webbing that attaches the second female connector of the second quick release buckle to the second end of the belt;

wherein the second ring and slider arrangement adjusts the effective length of the belt;

wherein the second ring and slider arrangement attaches to the second male connector and the third adjustment strap such that the span of the length of the second quick release buckle is adjustable.

9. The accessory for dispensing a chemical substance according to claim 8 wherein the plurality of primary holsters comprises a collection of individual holsters;

wherein each of the plurality of primary holsters are configured such that the sanitizer dispenses from the chemical container without requiring the removal of the chemical container from the selected primary holster.

10. The accessory for dispensing a chemical substance according to claim 9 wherein the first binding strap is a webbing;

wherein the first binding strap attaches to the pouch such that the first binding strap lays over the open face of the pouch;

wherein the second binding strap is a webbing;

wherein the second binding strap attaches to the pouch such that the second binding strap lays over the open face of the pouch.

11. The accessory for dispensing a chemical substance according to claim 10 wherein the first binding strap further comprises a first fastener;

wherein the first binding strap is further defined with a first free end and a first fixed end;

wherein the second binding strap attaches to the pouch such that the second binding strap lays over the open face of the pouch;

wherein the first fixed end is the end of the first binding strap that attaches to the pouch;

wherein the first free end is the end of the first binding strap that is distal from the first fixed end;

wherein the first free end remains unattached to the pouch until the first fastener attaches the first free end to the pouch;

wherein the second binding strap further comprises a second fastener;

wherein the second binding strap is further defined with a second free end and a second fixed end;

wherein the second fixed end is the end of the second binding strap that attaches to the pouch;

wherein the second free end is the end of the second binding strap that is distal from the second fixed end;

wherein the second free end remains unattached to the pouch until the second fastener attaches the second free end to the pouch;

wherein the first fastener is selected from the group consisting of a snap and a hook and loop fastener;

wherein the second fastener is selected from the group consisting of a snap and a hook and loop fastener.

12. The accessory for dispensing a chemical substance according to claim 11 wherein the plurality of primary holsters comprises a first holster and a second holster;
wherein a sewn seam attaches the first holster to the belt;
wherein a sewn seam attaches the second holster to the belt.

13. The accessory for dispensing a chemical substance according to claim 12
wherein the accessory for dispensing a chemical substance further comprises a shoulder harness;
wherein the shoulder harness further comprises one or more shoulder straps and one or more secondary holsters;
wherein the shoulder harness is a harness that attaches to the belt;
wherein the shoulder harness is worn over one or more shoulders of the healthcare worker such that the shoulder harness supports the belt;
wherein each of the one or more shoulder straps is a strap that secures the belt to a shoulder of the healthcare worker.

14. The accessory for dispensing a chemical substance according to claim 13
wherein the shoulder harness further comprises one or more shoulder straps and one or more secondary holsters;
wherein each of the one or more secondary holsters attaches to the one or more shoulder straps;
wherein each of the one or more secondary holsters are identical;
wherein each of the one or more secondary holsters is identical to any primary holster selected from the plurality of primary holsters.

15. The accessory for dispensing a chemical substance according to claim 14
wherein each of the one or more shoulder straps is a webbing structure that attaches to the belt;
wherein the one or more shoulder straps is selected from the group consisting of a cross strap and a plurality of shoulder straps.

16. The accessory for dispensing a chemical substance according to claim 15
wherein the cross strap is a webbing;
wherein the cross strap attaches to the belt at two locations;
wherein the cross strap further comprises a third holster;
wherein the third holster is a holster selected from the one or more secondary holsters that attaches to the cross strap.

17. The accessory for dispensing a chemical substance according to claim 15
wherein the plurality of shoulder straps further comprises a dexter strap, a sinister strap, a third holster, and a fourth holster;
wherein the dexter strap is a webbing;
wherein the dexter strap attaches to the belt at two locations;
wherein the sinister strap is a webbing;
wherein the sinister strap attaches to the belt at two locations;
wherein the third holster is a holster selected from the one or more secondary holsters that attaches to the dexter strap;
wherein the fourth holster is a holster selected from the one or more secondary holsters that attaches to the sinister strap.

* * * * *